United States Patent [19]

Coles et al.

[11] Patent Number: 5,164,590
[45] Date of Patent: * Nov. 17, 1992

[54] METHOD FOR EVALUATING CORE SAMPLES FROM X-RAY ENERGY ATTENUATION MEASUREMENTS

[75] Inventors: Mary E. Coles, Addison; Ernest L. Muegge, Grand Prairie, both of Tex.

[73] Assignee: Mobil Oil Corporation, Fairfax, Va.

[ * ] Notice: The portion of the term of this patent subsequent to Nov. 5, 2008 has been disclaimed.

[21] Appl. No.: 726,433

[22] Filed: Jul. 5, 1991

Related U.S. Application Data

[63] Continuation-in-part of Ser. No. 470,478, Jan. 26, 1990, Pat. No. 5,063,509.

[51] Int. Cl.$^5$ .................. G01V 5/00; G01N 23/06
[52] U.S. Cl. .................. 250/255; 250/269; 250/253; 378/5
[58] Field of Search ............ 250/253, 255, 265, 269, 250/252.1; 378/5, 4

[56] References Cited

U.S. PATENT DOCUMENTS

| | | | |
|---|---|---|---|
| 4,399,509 | 8/1983 | Hounsfield | 378/4 XR |
| 4,422,177 | 12/1983 | Mastronardi et al. | 378/17 |
| 4,649,483 | 3/1987 | Dixon, Jr. | 250/256 X |
| 4,688,238 | 8/1987 | Sprunt et al. | 378/4 |
| 4,722,095 | 1/1988 | Muegge et al. | 250/269 X |
| 4,782,501 | 11/1988 | Dixon, Jr. | 250/253 |
| 4,799,382 | 1/1989 | Sprunt et al. | 378/4 |
| 5,063,509 | 11/1991 | Coles et al. | 250/269 X |

*Primary Examiner*—Carolyn E. Fields
*Assistant Examiner*—Drew A. Dunn
*Attorney, Agent, or Firm*—Alexander J. McKillop; Charles J. Speciale; George W. Hager, Jr.

[57] ABSTRACT

X-ray attenuation measurements at two or more energies are carried out on core samples of earth materials for use in determining the relative contributions of Compton scattering and photoelectric absorption to the attenuation of the beams of X-rays by the samples. The measurements are utilized to calculate material bulk density, responsive to the difference in attenuation measured with respect to beams of two different X-ray energies and the attenuation of the beams of one of X-rays.

15 Claims, 6 Drawing Sheets

METHOD FOR EVALUATING CORE SAMPLES FROM X-RAY ENERGY ATTENUATION MEASUREMENTS

CROSS-REFERENCE TO RELATED APPLICATIONS

This application is a continuation-in-part of U.S. patent application Ser. No. 07/470,478 filed Jan. 26, 1990, now U.S. Pat. No. 5,063,509, filed Nov. 5, 1991.

BACKGROUND OF THE INVENTION

Computed tomography (CT) technology has been in use in the medical field for several years. Such CT scanning instruments produce a cross-sectional view through the subject material along any chosen axis. A two dimensional X-ray image of electron density variations within the object scanned is produced. The advantages of CT scanning over conventional radiography is found in its much clearer images and its superior resolution of variation in density of the object imaged.

In medical CT scanners, an X-ray source and a detector array circle a patient in a period of about 2 to 9 seconds and produce an image with maximum resolution of 0.25 mm in the X-Y plane. This plane can be moved in discrete intervals to obtain information in 3 dimensions. For more details of such medical CT scanners, reference may be made to U.S. Pat. No. 4,157,472 to Beck, Jr. and Barrett (assignee General Electric Company) and U.S. Pat. No. 4,399,509 to Hounsfield (assignee EMI Limited).

Many other applications of CT scanning can also be made. For example, CT scanning has been applied to the non-destructive testing of wood materials, such as for disease in living trees; see U.S. Pat. No. 4,283,629 to Habermehl. In a further application, CT scanning has been applied to the examination of non-living objects, such as motors, ingots, pipes, etc.; see U.S. Pat. No. 4,422,177 to Mastronardi et al (assignee American Science and Engineering, Inc.).

More recently, CT scanning technology has been applied to the field of energy research by way of petrophysical and reservoir engineering applications; see Wellington et al, "X-ray Computerized Tomography", *Journal of Petroleum Technology*, pages 885–898, August, 1987. Wellington et al describe generation of images of core samples from particular formations of interest. Wellington et al effectively acknowledge in FIG. 6 and discussion thereof, however, that the bulk density map of a core sample can be calculated accurately only if one already knows the lithology of the core material, that is, one must know the composition of the core in advance. This is a very substantial limitation on the use of CT scanning in analysis of rock samples.

More particularly, Wellington et al describes generation of images of core samples by CT scanning. However, Wellington et al acknowledges that to do so requires that one already know the lithology of the sample. This is often not possible. This is because it is impossible in many cases to examine core samples without destroying them. As noted by Wellington et al at page 889, such samples typically amount to unconsolidated samples of sand, frozen within opaque plastic tubes or the like. If the sample is removed from the tube, it typically collapses, destroying any structural integrity it may have had. This prevents determination of the bulk density $\rho$, and destroys highly relevant permeability and porosity information as well. No acceptable method for removing a "plug" from the core without compromising its structural integrity is known. Even if a particular sample itself is relatively consolidated, infiltration by drilling mud, for example, which commonly varies with depth, will interfere with density measurement. Thus, in general, accurate measurement of the density of a given undisturbed core sample is of primary interest in analysis thereof with respect to the search for oil and gas or the production of oil and gas from known reservoirs thereof.

Processes involved in coal gasification and combustion have been monitored using time-lapse CT imagery to observe changes in density (e.g., due to thermal expansion, fracturing, emission of gases, consumption of combustion) during progressive heating in a controlled atmosphere. Core flooding experiments can now be carried out with CT scanning to aid in enhanced oil recovery and fluid mobility control. For example, the permeability of materials within core samples to various fluids at varying conditions of temperature and pressure can be determined. Such experiments might involve flushing a fluid through a core sample and monitoring the shape of the fluid front. By subtracting the images of the cores before and after flooding, the exact shapes of the fluid front can be determined. Such core flood experiments allow the interior of the core sample to be observed without disturbing the sample. The sweep efficiency and flow paths of fluid of interest may then be studied on the scale of millimeters. Typically, the penetration of X-rays allows experiments to be performed with up to 4 inch diameter core samples. Relatively porous samples of somewhat greater dimension can also be analyzed.

Drilling fluids can usefully be analyzed by CT scanning, as such fluids are characterized by high density brines, various organics and several compositionally different weighing agents. Formation damage can also be investigated since CT scanning can detect infiltration of drilling mud, absorption of organics and the reversibility of completion fluid penetration. Shale oil recovery can be aided as CT scanning could detect penetration by solvents and could directly measure structure changes on retorting. Rock fractures can be identified.

U.S. Pat. No. 4,649,483 to Dixon discloses a method for determining fluid saturation in a porous medium through the use of CT scanning. Multi-phase fluid saturation in a sample of a porous medium is determined through computer tomographic scanning. The sample is scanned with X-rays of differing energies in both the fluid saturated and the fluid extracted states. Each of the extracted fluids is also scanned at differing X-ray energies. The computed tomographic images produced are utilized in the determination of the X-ray mass attenuation coefficients for the sample and the extracted fluids. From these mass attenuation coefficients, the weight fractions and volume fractions of each of the extracted fluids are determined.

U.S. Pat. No. 4,688,238 to Sprunt et al discloses a method for using CT scanning over a range of confining pressures on a core sample to determine pore volume change, pore compressibility and core fracturing. A core sample with a surrounding elastic jacket is placed in a confining pressure cell. Pressure is applied to the cell to press the jacket into contact with the surface of the sample. The pressure in the cell is increased stepwise over a plurality of pressure points. The sample is scanned at a plurality of locations with X-rays at each of the pressure points. Computed tomographic images of the sample are produced for each of the X-ray scans. The conformance of the jacket to the sample is determined from these computed tomographic images. From such conformance, a range of confining pressures is determined over which pore volume and pore compressibility of the sample are measured without being affected by improper conformance of the jacket to the surface of the sample. Also rock fracturing is determined from the pressure at which crushing of the sample destroys permeable channels within the sample and results in impermeability of the sample.

U.S. Pat. No. 4,722,095 to Muegge et al discloses a method for identifying porosity and drilling mud invasion of a core sample from a subterranean formation. A gas is supplied to the core sample at a first pressure. The gas is thereafter allowed to expand from the core sample until equilibrium is reached. The volume of the gas which expands from the core sample is measured. A second pressure is measured in the core sample after the gas has expanded. The pore volume of the core sample is determined from such first and second pressures and such measured gas volume. Bulk volume of the core sample is measured. Porosity of the core sample is determined from the ratio of the pore volume to the bulk volume. The core sample is scanned with X-rays and computer tomographic images produced. The concentration of drilling mud solids in the core sample is identified from the density effect of the drilling mud solid on the computer tomographic images. The porosity determination is corrected for the volumetric concentration of drilling mud solids in the pore spaces of the core sample. The X-ray scanning is calibrated to a density scale based on the barite content of the drilling mud, the barite having a higher grain density than the remaining minerals forming the core sample. This X-ray scanning is preferably calibrated by adjusting the computed tomographic number scale in Hounsfield units to a zero level based on the numerical measure of the X-ray absorption property of barite.

U.S. Pat. No. 4,799,382 to Sprunt et al discloses a method for measuring reservoir characteristics of a core sample from a subsurface formation by subjecting the core sample to pressure cycling. Pore volume changes during such pressure cycling are measured. Pore compressibility is determined from a plot of the measured pore volume change versus pressure. The core sample is scanned with X-rays at least once for each pressure cycle and a computed tomographic image is produced. From the plurality of produced images, a determination is made of the pressure at which fracturing initiated and of the location or locations within the sample at which fracturing occurs.

U.S. Pat. No. 4,782,501 to Dixon discloses a method for determining the porosity and pore compressibility of a core sample of a porous media by the use of X-ray scanning in the presence of confining pressure. The porosity of the core sample is determined at atmospheric reference pressure (i.e., zero confining stress). The sample is then saturated with a fluid of predetermined X-ray attenuation coefficient. The fluid saturated sample is placed in a confining pressure cell and scanned with X-rays at a plurality of points along the sample. A first set of computed tomographic images are produced at the plurality of points along the sample. A first set of computed tomographic images are produced at the plurality of points along the sample. From these images, an X-ray attenuation coefficient at zero confining stress is determined. The pressure is then increased within the cell to provide confining stress to the sample. The sample is then scanned with X-rays at a plurality of points along the sample. A second set of computed tomographic images are produced at said plurality of points along the sample for the confining stress. From these images, an X-ray attenuation at confining stress is determined. Porosity is then determined at confining stress from the determinations of sample porosity at zero confining stress, saturating fluid X-ray attenuation coefficient, sample X-ray attenuation coefficient at zero confining stress, and sample X-ray attenuation coefficient at confining stress.

SUMMARY OF THE INVENTION

It is a principal object of the present invention to provide a method for determining the density $\rho$ of a core sample of essentially unknown composition.

It is a further object of the invention to provide a method for imaging a cross-sectional "slice" through a core sample, in which the constituents of the core sample, including residual oil, surfactant foams, drilling muds and the like, as well as the rock itself, can be identified responsive to accurate measurements of their density.

It is a further object of the invention to provide a synthetic density log of a core sample having improved resolution and accuracy as compared to logs in the prior art.

The attenuation of beams of X-rays in a particular range of energy by samples is a function of two attenuation mechanisms, "Compton scattering" and "photoelectric absorption". Compton scattering accounts for most of the total attenuation when the sample comprises materials of relatively low atomic weight. However, where the materials have relatively higher atomic weights, such as dolomites or other carbonate materials of geological interest, or contain barites, commonly used as additives in drilling mud, the photoelectric absorption mechanism starts to come into play.

In accordance with the present invention, a method is provided for determining the relative contributions of Compton scattering and photoelectric absorption to the total X-ray attenuation of core samples of earth materials using beams of X-rays at two or more different scanning energies, and for thereafter calculating the bulk density of the scanned material using the differences in attenuation between the beams of X-rays of two differing energies and the measured X-ray attenuation for one of the X-ray energies.

More particularly, a first set of material samples are selected with differing known densities and having low atomic numbers, such that X-ray attenuation takes place therein primarily due to Compton scattering. These samples are scanned with beams of X-rays of two different energies and the attenuation of each beam due to Compton scattering is measured. The relationship of these X-ray attenuation measurements to bulk density is determined for each of the X-ray energies. Thereafter, a second set of material samples are selected with differing known densities and having higher atomic numbers, such that both Compton scattering and photoelectric attenuation contribute to the total attenuation of the beams of X-rays. These samples are also scanned with beams of X-rays of two different energies and the attenuation of these beams, attributable to both Compton scattering and photoelectric attenuation, is measured. The contribution of Compton scattering to the total attenuation of the beams measured with respect to the second set of samples is calculated from their bulk densities, employing the relationship of X-ray attenuation to bulk density determined with respect to the first set of samples. The photoelectric contribution to the attenuation of the beams by the second set of samples is then calculated, by subtracting the calculated Compton scattering attenuation from the total X-ray attenuation measurements for each of the second set of samples.

In subsequent determination of the bulk density of a sample of interest, the sample is again scanned with beams of X-rays of two different energies. The difference in the measured attenuations between the beams of X-rays at two different energies, and the measured attenuation for one of the beams of X-rays can then be used to determine the bulk density of the sample of interest in accordance with the relations derived with respect to the first and second sets of samples of known density.

The bulk density can be measured with the source and detector disposed at varying locations with respect to the sample. These measurements can be used in accordance with known CT image processing techniques to generate a cross-sectional image of the sample of interest.

Such bulk density information can be used, for example, to characterize the quality of surfactant foams used to enhance oil recovery; to characterize the disposition of residual oil in a formation; to construct a synthetic log of a well, which may be correlated with logging information derived from other logging instruments; and for other purposes.

DESCRIPTION OF THE PREFERRED EMBODIMENTS

Before describing the method of the present invention for the dual energy X-ray scanning of a material sample and the use of the X-ray attenuation measurements from such scanning to calculate the bulk density of the sample, a brief description will be set forth of a CT scanning system which may be employed for X-ray scanning and attenuation measurements.

Figure 1:
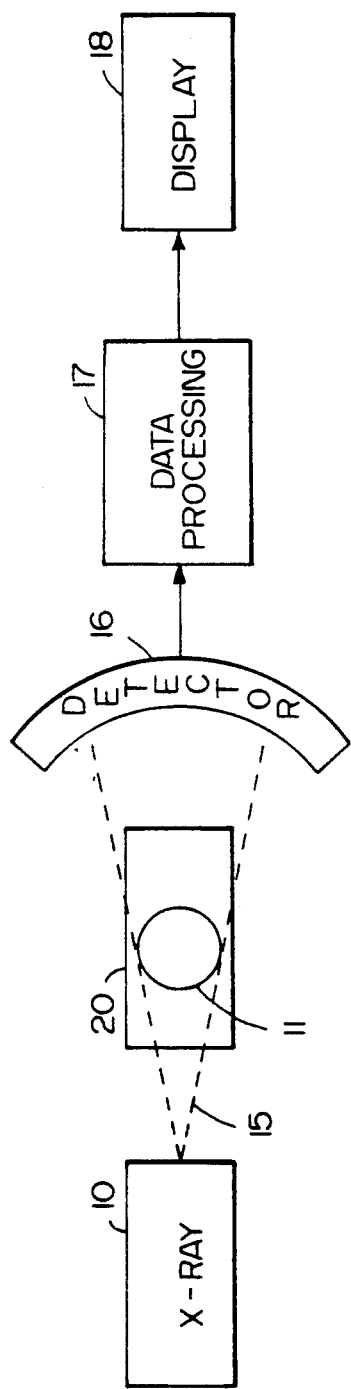
FIG. 1 is a pictorial view of a CT scanning system for use in scanning a material sample with X-ray energy.

Referring now to FIG. 1, X-ray energy provided by an X-ray tube 10 passes through the core sample 11 and falls on the detector array 16. Rotation of the core sample within the X-ray fan beam 15 is provided by a gantry 20. In an alternative embodiment, the core sample 11 may remain stationary and the gantry may be used to rotate the X-ray tube 10 and detector 16 about the core sample. In medical applications, CT scans on the order of 2 to 9 seconds long are used. However, patient dose limitations are of no concern in the present application and scan times of the core sample can be up to 30 seconds per scan, or even longer, if desired. The output of the detector array 16 is processed in a manner generally understood in the art by the data processor 17 to provide an output on the display 18. After a desired number of scans are completed for a core sample slice, the sample is indexed one slice-width through the X-ray fan beam to place the next adjacent sample slice within the path of the X-ray fan beam. In this manner, a 3-D tomographic presentation is made on the display 18 of the entire sample by compositing the cross-sectional view of each of the scan slices. As indicated, the processing of the output of the detector 16 by the processor 17 to yield an image for display is well understood in the art.

A particularly suitable X-ray tube 10 used for CT imaging is the Elscint Excel 2002 translate-rotate body scanner with a Telefunken C-6000 stationary anode-cathode X-ray tube and 280 cadmium tungstate scintillation detectors coupled to solid state photodiodes. The peak X-ray acceleration voltage is 140KV at 40.0 mA. The spatial resolution is 20 line pairs per cm. The pixel (picture element) size at Zoom 1 (512×512) ranges from 0.265 mm to 0.94 mm and at Zoom 4 (512×512) ranges from 0.065 mm to 0.23 mm, the pixel size varying with scan and circle diameter and reconstruction zoom factor.

A particularly suitable detector array 16 for use in the present invention for 100 micron resolution would comprise a 1024×1 linear array of photodiodes on 0.001 inch center-to-center spacing with pixel (picture element) apertures of 0.001 inch by 0.1 inch. An example of such an array is the Reticon 1024S fiber optic faceplate. For a lower 250 micron resolution, a 200×1 linear array of photodiodes on 0.01 inch center-to-center spacing with pixel apertures of 0.01 inch to 0.01 would be suitable. An example of such an array is that used in digital mammography equipment supplied by Bio-Imaging Research, Inc.

Optically coupled to the input surfaces of the photodiode arrays are scintillation arrays comprised of a plurality of discrete scintillators having X-ray sensitive fluorescent materials individually optically coupled to the input surfaces of the discrete photodiodes. Such materials may comprise $CdWo_4$, $C_sI$, $GdOBr$ or $LaOBr$, among others. Such a combination of scintillators and photodiodes provides for a complete scintillation counter. The photodiodes provide electrical signals whose heights are proportional to the X-ray energy falling upon the surfaces of the scintillators. After suitable amplification, the signals are digitized for use in producing a desired tomographic display.

The recorded digital image is composed of individual image units arranged in a matrix. Computer tomography images consist of maps of linear X-ray attenuation coefficients within the object being imaged. On standard black and white images, each pixel contains discrete information that corresponds to a spectrum of tonal values on a greyness scale ranging from black to white. These gray scale values conventionally correspond to CT image density values on the Hounsfield scale ranging from low density ($-1000$) to high density ($+3095$).

For a more detailed description of CT scanning systems which may be utilized in the method of the present invention, reference may be made to each of the aforementioned U.S. patents and the Wellington et al *Journal of Petroleum Technology* article discussed above. The teachings of these documents are incorporated herein by reference.

Conventionally, in medical CT scanning, a water sample is used as an X-ray attenuation standard. When higher attenuation core samples of each materials are scanned, secondary standards are utilized as reference attenuating media. These reference media must be of uniform composition and density and should exhibit X-ray attenuation characteristics similar to those of the material to be scanned. Examples of such reference materials are aluminum and fused quartz. Fused quartz is uniform in composition and has density and X-ray attenuation close to that of many sandstones. For solid materials (sandstones, fused glass beads, quartz and aluminum) there is a single linear function relating measured attenuation (CT number) to bulk density. This is because such solid materials, as well as water, are composed of atoms having relatively low atomic numbers which cause such materials and water to exhibit low photoelectric attenuation. Consequently most of the X-ray attenuation results from Compton scattering, so that the measured attenuation is a simple linear response function of the density. Bulk density can accordingly be calculated from single energy X-ray attenuation measurements using this simple linear response function.

However, as the atomic number of a material increases, such as with chlorides, bromides and iodides, the photoelectric contribution to X-ray attenuation increases. That is, X-rays are absorbed by these higher atomic weight materials according to the photoelectric effect as well as due to Compton scattering, and the photoelectric absorption increases with increase in the atomic number of the material of the sample. Even though the total attenuation by a given material remains a simple linear response function of the incident energy, the slope of this function increases with increasing photoelectric contribution to total attenuation. Consequently material samples of relatively higher atomic weights, that is, exhibiting substantial photoelectric contribution to the total attenuation of a beam of X-rays, cannot be accurately described by a linear response function having a single slope, but must be calibrated against a material sample of similar lithology which must be uniform in density and composition.

To determine the density of a sample using a single X-ray attenuation measurement of X-rays at a single energy, as disclosed in the Wellington et al reference, therefore requires that appropriate standards be made available to characterize the response curve, and that there be sufficient knowledge of the material to characterize it as to composition, in particular its effective atomic number.

The requirement that the composition of a material be known before its density can be determined severely limits the utility of the single energy X-ray scan technique of Wellington et al. Many core samples from earth formations are inhomogenous, containing heavier elements such as anhydride or dispersed pyrite. Infiltration of unknown amounts of drilling mud, as typically occurs, further prevents accurate density measurements using the Wellington process. The method of Wellington et al therefore cannot be employed to determine the density of such samples, or to image core samples containing non-rock materials. It would be very useful to be able to provide images of core samples containing residual oil, surfactant foams, drilling muds, and other constituents, in which the constituents were accurately characterized by measurement of their density.

As noted above, it is therefore a specific object of the present invention to overcome these limitations of the single energy X-ray scan, in particular to eliminate the requirement that the material composition be known.

The method of the present invention achieves this objective through the performance of two or more X-ray scans, utilizing beams of X-rays of differing energies, of several different materials of known composition and density. The attenuation of the beams by the material samples are measured. The resulting attenuation measurements are used to accurately describe the relative photoelectric and Compton scattering contributions to the attenuation of the beams of X-rays of differing energies by the particular materials. This allows the calculation of bulk density for such earth materials as limestone and dispersed pyrite sandstone (which exhibit high photoelectric attenuation) in addition to clean sandstone (low photoelectric attenuation). Such a method for utilizing X-ray scanning accommodates changes or non-uniformity in the chemical composition of the core sample. This in turn allows the determination of the densities of a wide range of core samples taken from subterranean earth formations containing heavier minerals as well as other constituents. This is highly useful in characterizing possible hydrocarbon (i.e., oil or gas) reservoirs.

Scanning a material sample with beams of X-rays of differing energies, e1 and e2, and measuring the attenuation of the beams, expressed in terms of CT numbers, provides the following expressions for the photoelectric and Compton scattering contributions to the total measured X-ray attenuation:

$$CT_t^{e1} + CT_p^{e1} + CT_c^{e1} \tag{1}$$

and $$CT_t^{e2} = CT_p^{e2} + CT_c^{e2} \tag{2}$$

where the superscripts indicate the scanning energies e1 and e2, and the subscripts refer to the total attenuation t, and to the photoelectric p and Compton scattering c contributions to the total attenuation.

Figure 2:
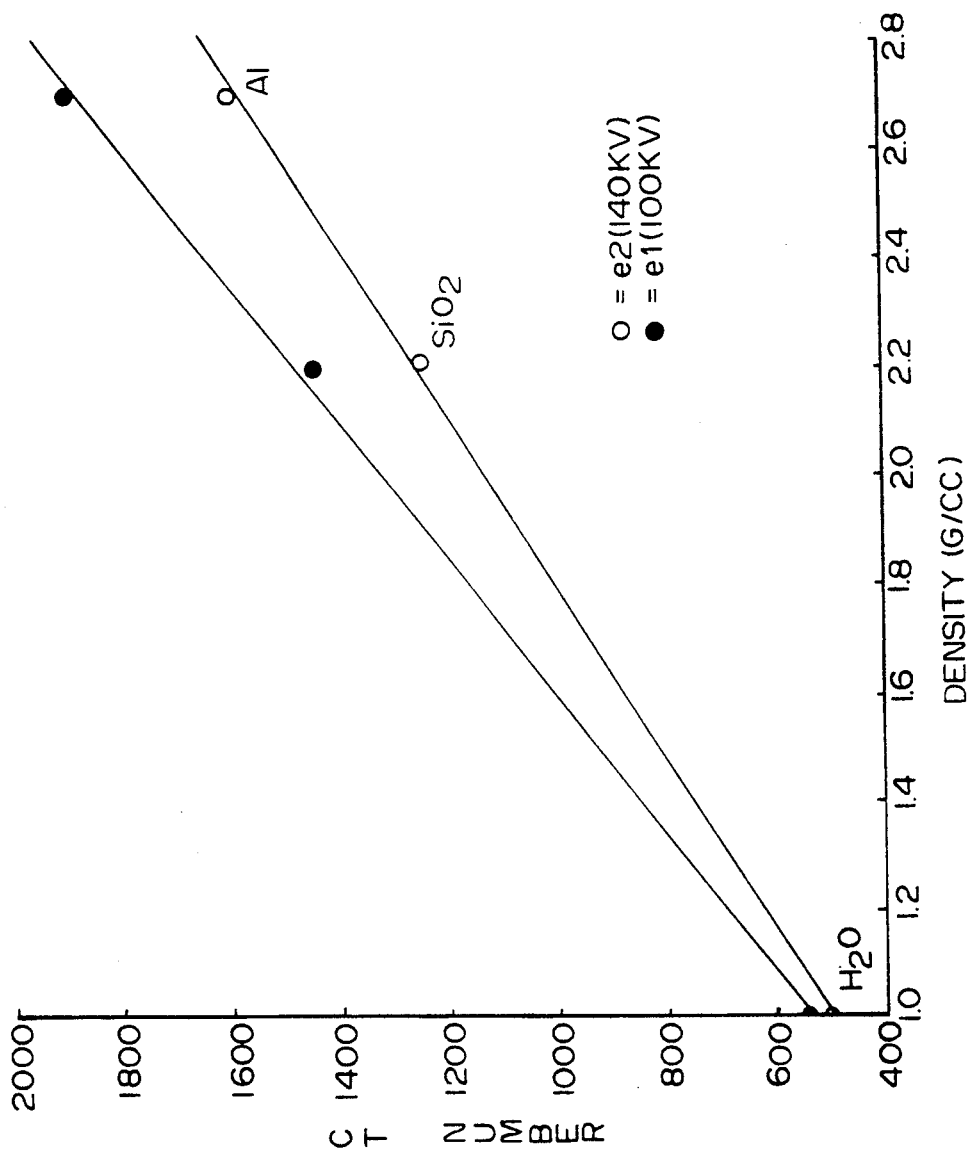
FIGS. 2, 3, 4 and 5 are plots of X-ray attenuation measurements made by the CT scanning system of FIG. 1 in accordance with the method of the present invention for determining the photoelectric and Compton scattering contributions to total X-ray attenuation as well as bulk density.

Water, quartz and aluminum standards, among others, are composed of elements of low atomic number and in the energy range of interest will attenuate X-rays primarily by Compton scattering. That is, $CT_p \simeq 0$ for those materials. Their attenuation of the X-rays is described by a linear function of the bulk density of the material. FIG. 2 is a plot of the attenuation of beams of X-rays of 100 KV and 140 KV (expressed as CT number) versus the density of a number of low atomic number materials, and illustrates the linear nature of this relationship.

The linear nature of the attenuation response of these materials may be used to approximate the X-ray attenuation arising from Compton scattering of other (non-standard) materials as follows:

$$CT_c^{31} = (a1)(\rho) - b1 \tag{3}$$

and $$CT_c^{e2} = (a2)(\rho) - b2 \tag{4}$$

where a1, a2, b1 and b2 are constants defining the linear relationship of equations (1) and (2) above and $\rho$ is the bulk density of the material. For the materials of FIG. 2, the linear functions of equations (3) and (4) become:

$$CT_c^{100KV} = 797.541\rho - 269.498 \tag{5}$$

and $$CT_c^{140KV} = 636.550\rho - 142.080 \quad (6)$$

The total CT attenuation of several materials measured at 100 KV and 140 KV are listed in Table 1.

TABLE 1

| Material | Density (g/cc) | CT# (140 KV) | CT# (100 KV) |
|---|---|---|---|
| 1. H$_2$O | 1.0000 | 500.0 | 540.0 |
| 2. NaBr | 1.0300 | 678.7 | 801.3 |
| 3. NaBr | 1.0900 | 901.2 | 1135.6 |
| 4. NaI | 1.1030 | 1581.8 | 2268.9 |
| 5. NaBr | 1.1800 | 1200.2 | 1609.9 |
| 6. NaCl | 1.1970 | 684.9 | 777.9 |
| 7. NaI | 1.2000 | 2203.4 | 3429.4 |
| 8. CaCl$_2$ | 1.2378 | 779.4 | 943.5 |
| 9. NaBr | 1.2700 | 1450.3 | 2032.2 |
| 10. NaBr | 1.3600 | 1666.4 | 2412.7 |
| 11. CaCl$_2$ | 1.4428 | 1029.0 | 1258.1 |
| 12. Fused Glass Beads 1A | 1.7600 | 1035.7 | 1221.9 |
| 13. Fused Glass Beads 5 | 1.8300 | 1112.6 | 1298.2 |
| 14. Fused Glass Beads 2A | 2.1100 | 1267.6 | 1488.5 |
| 15. Kel-F Teflon | 2.1300 | 1240.3 | 1461.7 |
| 16. Fused Quartz | 2.1960 | 1241.5 | 1445.4 |
| 17. Fused Glass Beads 4 | 2.3100 | 1358.3 | 1616.0 |
| 18. Fused Glass Beads 3 | 2.3200 | 1375.2 | 1612.2 |
| 19. Al | 2.7000 | 1588.2 | 1918.2 |

[All CT values shifted by 1000 to eliminate negative signs.]

Figure 3:
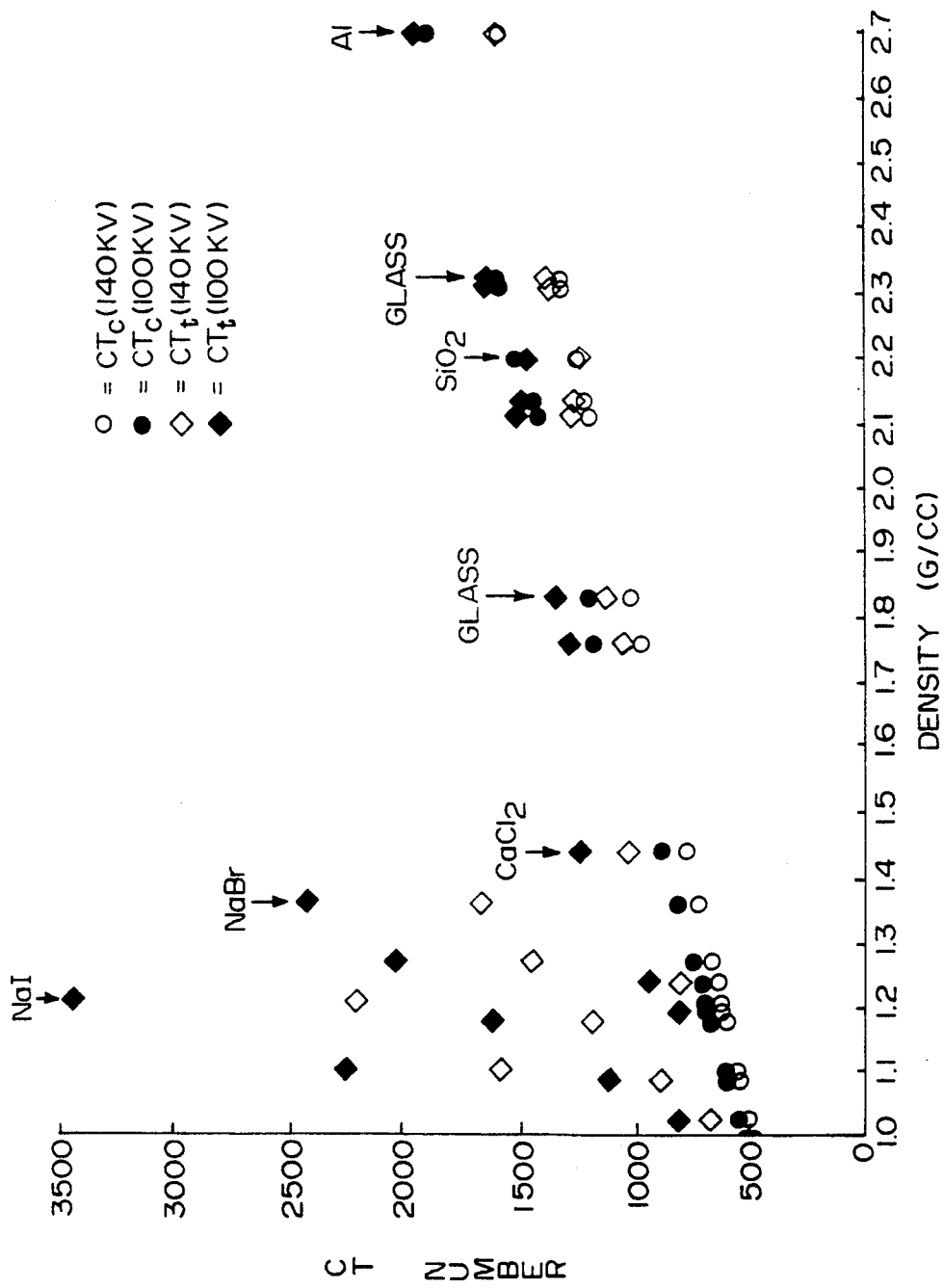

The total CT attenuation $CT_t$ as listed in Table 1 and the attenuation $CT_c$ attributed to Compton scattering as calculated from eqs. (5) and (6) for a number of materials are plotted in FIG. 3. FIG. 3 illustrates the difference between the attenuation $CT_c$ due to Compton scattering, shown as circles, and the total attenuation $CT_t$, shown as diamonds, for a number of different materials. The symbols shown in outline relate to attenuation of a beam of 140 KV X-rays, and those filled in to attenuation of a beam of 100 KV X-rays. As illustrated, the spacings of the symbols are very close for materials of low atomic weight, such as various glasses, SiO$_2$, and aluminum, indicating that for these materials the attenuation is largely due to Compton scattering and thus is a function of their density. By comparison, FIG. 3 shows that for higher molecular weight materials such as NaI and NaBr the differences are much greater, indicating that in these relatively high atomic weight materials, photoelectric absorption makes a major contribution to the total attenuation.

Rearranging the terms of equations (1) and (2), the photoelectric contribution $CT_p$ for materials having higher atomic numbers may be calculated as follows:

$$CT_p^{e1} = CT_t^{e1} - CT_c^{e1} \quad (7)$$

and $$CT_p^{e2} = CT_t^{e2} - CT_c^{e2} \quad (8)$$

Figure 4:
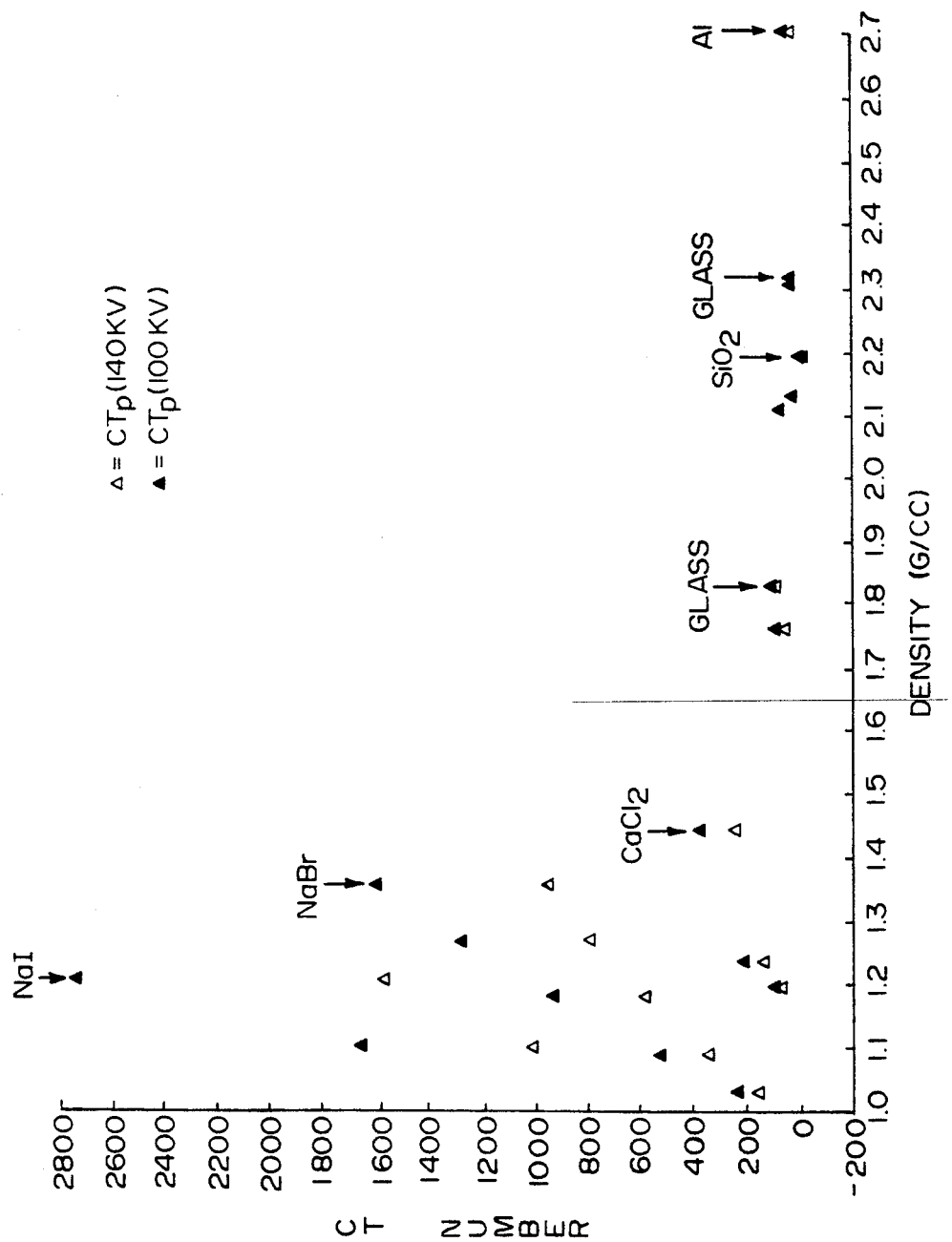

The photoelectric contributions to the total attenuations listed in Table 1 have been calculated from eqs. (7) and (8) and are plotted in FIG. 4 (only a few of the materials being identified by name or symbol). That is, FIG. 4 shows the actual values for the photoelectric contribution $CT_p$ represented by the spacing of the symbols in FIG. 3, graphically demonstrating that $CT_p$ is very small with respect to the low atomic weight materials and much greater in the case of the high atomic weight materials. FIG. 4 also demonstrates that the total attenuation is a linear function solely of density for the low atomic weight materials, and that the total attenuation by the higher atomic weight materials is not exclusively a linear function of density.

Figure 5:
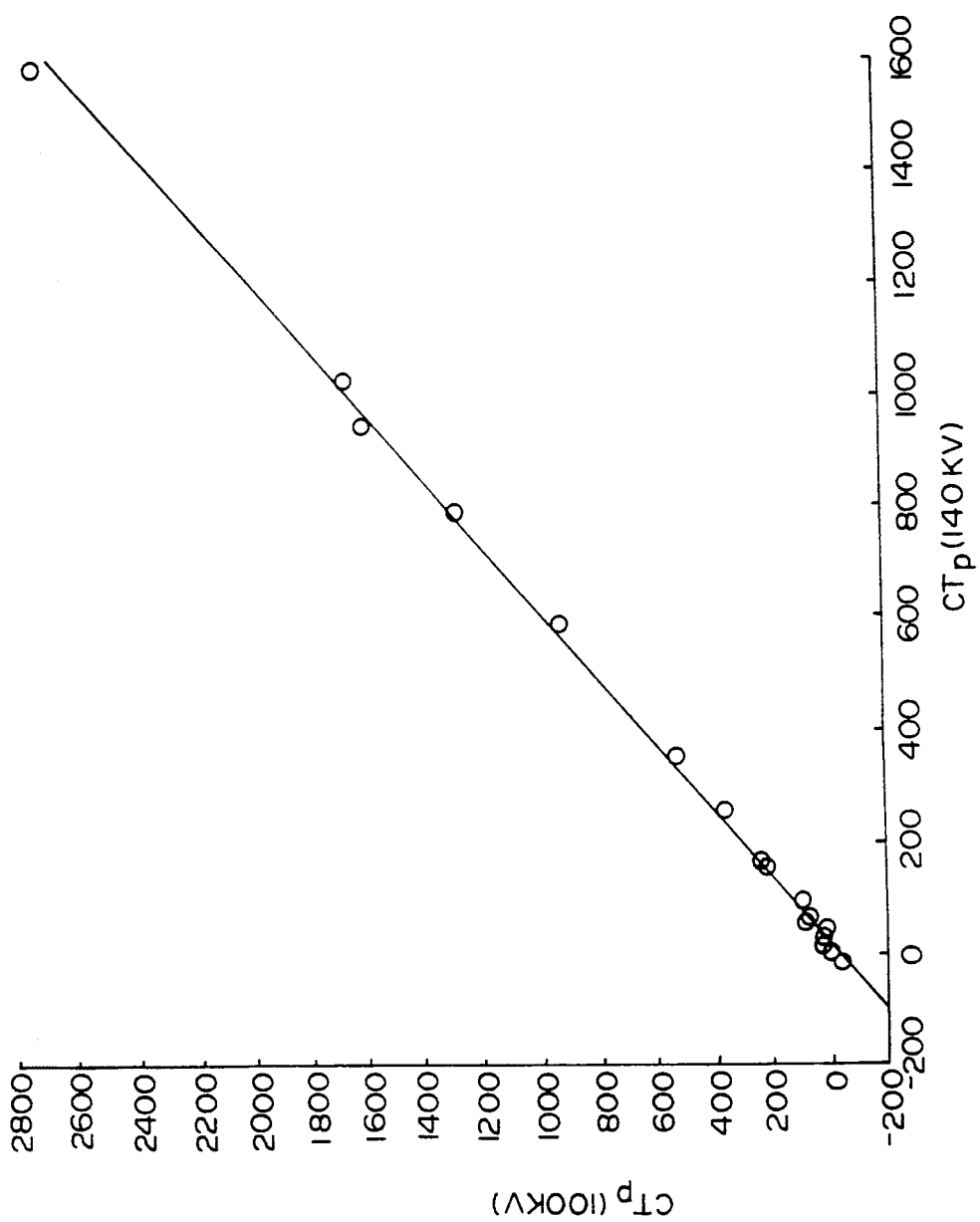

Finally, FIG. 5 demonstrates that there is a linear relationship between the attenuation due to photoelectric absorption of two beams of X-rays of two energies used to irradiate any particular sample. More specifically, plotting the photoelectric contributions to the total attenuation at one energy with respect to another energy reveals a linear relationship, shown in FIG. 5, and having the general expression:

$$CT_p^{e1} = (c)CT_p^{e2} - d \quad (9)$$

where c and d are constants defining the linear relationship, and effectively calibrate the measured values for the particular X-ray apparatus. This linear relationship of the plot of FIG. 5 is expressed as:

$$CT^{100KV}_p = (1.71)CT^{140KV}_p - 28.047 \quad (10)$$

Subtracting equations (1) and (2) yields:

$$CT_t = CT^{e1}_p - CT^{e2}_p + CT^{31}_c + CT^{e2}_c \quad (11)$$

where $\Delta CT_t$ is the difference in CT number ($CT^{e1}_t - CT^{e2}_t$), that is, the difference in total attenuation, measured with respect to the two beams of X-rays at scanning energies e1 and e2.

Subtracting equation (4) from equation (3) and substituting into equation (11) yields:

$$\Delta CT_t = CT^{e1}_p - CT^{e2}_p + a3\rho - b3 \quad (12)$$

where
a3 = a1 − a2 and
b3 = b1 − b2.

Using the expressions of equations (6) and (5) for equations (4) and (3) respectively, equation (12) becomes:

$$\Delta CT_t = CT_p^{100KV} - CT_p^{140KV} + 160.991\rho - 127.416 \quad (13)$$

Substituting equations (9), (8) or (7) and (4) or (3) sequentially into equation (12) and rearranging terms yields the following general bulk density expression:

$$\rho = (\Delta CT_t - f(CT_t^{e'}) + g)/h \quad (14)$$

where f, g and h are constants and $CT_t^{e'}$ is the attenuation measured at one of the energies e1 or e2.

With e2 being the selected energy for e', equations (10), (8) and (6) are substituted into (13) and terms rearranged. Equation (14) then becomes:

$$\rho = (\Delta CT_t - 0.7086 CT_t^{140KV} + 54.783)/ - 290.068 \quad (15)$$

The constants f, g and h are determined in solution of equation (14) with respect to known sample materials, that is, after measurement of the attenuation of two beams of X-rays by samples of both low and high atomic weight materials. Given f, g and h, the bulk density ρ of a sample of interest can be calculated directly using equation (15), upon measurement of the total attenuation $CT_t$ at two energies e1 and e2.

As an example of the practice of the invention, scanning a berea core sample results in a measured CT value of 1208.30 CT units at 140 K scanning energy, and a measured CT value of 1415.30 units at 100 K scanning energy. The change in measured CT number is 207. The calculated density from Equation (15) becomes:

$$\rho = [207 - 0.7086(1208.3) + 54.783]/-290.068 = 2.05 \quad (16)$$

Alternatively, with e1 being selected for e', equations (10), (7) and (5) are substituted in equation (13) and terms rearranged. Equation (14) then becomes:

$$\rho = \Delta CT_t - 0.4147 CT_t^{100KV} + 32.073)/-169.258 \quad (17)$$

and calculated density becomes $$\rho = [207 - 0.4147(1415.30) + 32.073]/-169.25 = 2.05 \quad (18)$$

It will thus be appreciated that according to the basic technique of the invention, a sample of unknown composition is examined using plural beams of X-rays of differing energies, and the results are employed, using linear relations developed with respect to first and second sets of samples of known density, to calculate the density of the sample of interest.

More specifically, according to the invention, a first plurality of samples of relatively low atomic weight are irradiated with first and second beams of X-ray of differing energies. The attenuation of each of the beams is measured. The attenuations measured are used to determine the parameters defining a linear relation (e.g., equation 5 or 6) between the attenuation of X-rays due to Compton scattering in the first plurality of samples and their bulk density. A second set of samples of higher atomic weight and known densities are then similarly irradiated with two beams of X-rays of different energies. The measured attenuations are then used to define a second linear relation (e.g., equation 10) between the attenuation of X-rays due to photoelectric absorption in the second set of samples and the energy of the X-rays. Given these two linear relations, a third relation (e.g., equation 13 or 15) can then be derived relating the density of the sample to the total attenuation measured with respect to the two beams of X-rays. This can then be employed to determine the density of a sample of interest after irradiation with beams of energy of X-rays of two different energies.

The measured values for the densities of the sample can be employed in many useful ways in exploration for oil and gas and also in determining the proper steps to take in production of wells. For example, the apparatus of FIG. 1 is described in connection with generating a complete image of a cross-sectional section of a core sample. This is done in the prior art by measuring the attenuation of the incident X-rays at a large number of locations within a cross-sectional "slice" of the core sample, and combining these according to known tomographic imaging processes to yield a complete image of the "slice". According to the invention, the attenuation values measured can be replaced in each picture element or "pixel" of the image by gray scale values accurately corresponding to the density of the material at the corresponding location in the "slice". Such a cross-sectional view of the undisturbed core sample is very useful in determining whether and how to produce the formation.

For example, consider the recovery of residual oil. Residual oil is that oil which remains adhered to the rock grains in a porous formation after the bulk of the oil has been recovered. The residual oil is directly depicted in bulk density images made according to the invention as summarized above. Such images are very useful in understanding the distribution of the residual oil and in its recovery. For example, it is understood that in general residual oil tends to collect in the larger pores in a structure, but the process is difficult to model in the laboratory and it is impossible to directly inspect the cores without destruction of their structural features. By imaging the core according to the invention, the distribution of the residual oil within the sample can be accurately identified and correlated to rock structural characteristics, enabling improved understanding and improved recovery of the residual oil.

A further use of the method of the invention in recovery of oil is in determining the efficacy of the use of surfactant foams. Such foams, typically surfactants in water, are commonly used to "clog" highly permeable formations to improve the efficiency of water-flooding techniques for enhanced recovery. It is generally understood that a foam having smaller bubbles and thus greater surface area is more useful than one having larger bubbles and less surface area. Again, it is difficult to monitor accurately the formation of such foams in a laboratory under appropriate core conditions.

According to the invention, one can place a core sample in the laboratory under conditions similar to those encountered in the formation, introduce a particular foam of interest, and image the disposition and behavior of the foam within the formation, to determine whether it is performing as anticipated. More particularly, for example, it is possible to add the foam constituents at one end of an elongated core sample, pressurize the core, and make images of the cross-section of the core sample at intervals along its length, and possibly at intervals of time, to monitor motion of the foam through the core. Alternatively, one could inject a foam into one portion of a core, pressurize the core and possibly control its temperature to be similar to conditions in the formation, and form images of the same "slice" of the core over time, to determine whether the foam penetrates the core, and if so, with what effect.

There are other uses of the method of the invention which do not involve image generation directly. For example, it is commonplace to "log" a well prior to or during production with any of a wide variety of instruments. That is, any of a wide variety of logging instruments can be lowered progressively into a well. Variations in the signal response provide a picture of the geological structure surrounding the wellbore. Many such instruments are responsive to variation in density of the structure; however, many of the most useful of these instruments have a vertical resolution of only about one foot. In numerous areas of interest, the subsurface strata may be only on the order of one inch thick, so that they cannot be imaged by such logging instruments. According to the invention, one can image cross-sectional "slices" through an undisturbed core sample at much shorter intervals, e.g., 3, 6 or 12 mm and by comparing these determine the precise location and thickness of various bands in the strata. Since according to the invention accurate values for the density of the material are provided, this information can be used directly to determine the material surrounding the formation.

Figure 6A:
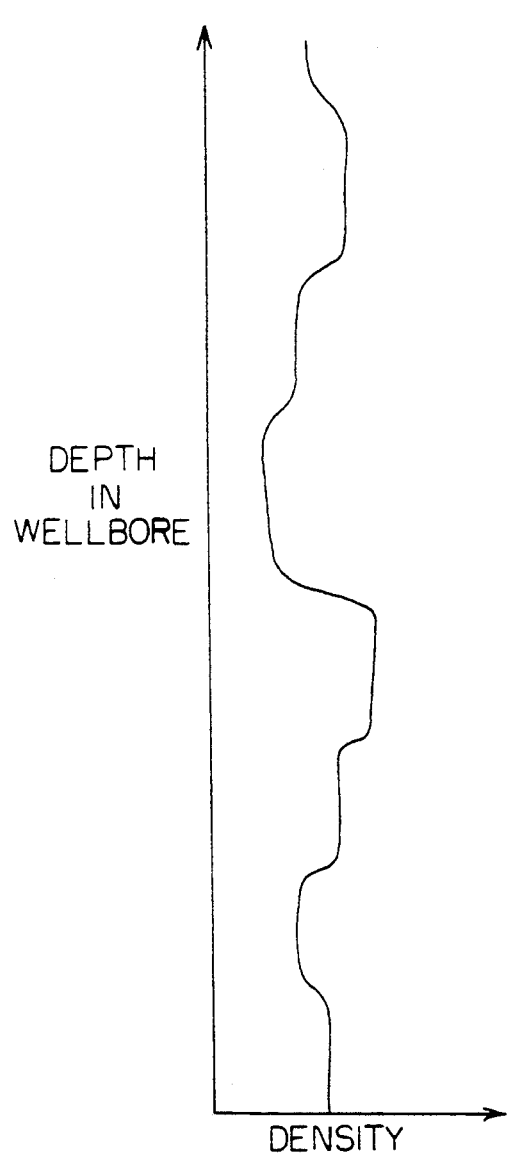
FIGS. 6(a) and 6(b) show comparative logs of the density of the formation surrounding a wellbore, derived using a conventional logging tool, and of a core sample, derived using the method of the invention, respectively.
Figure 6B:
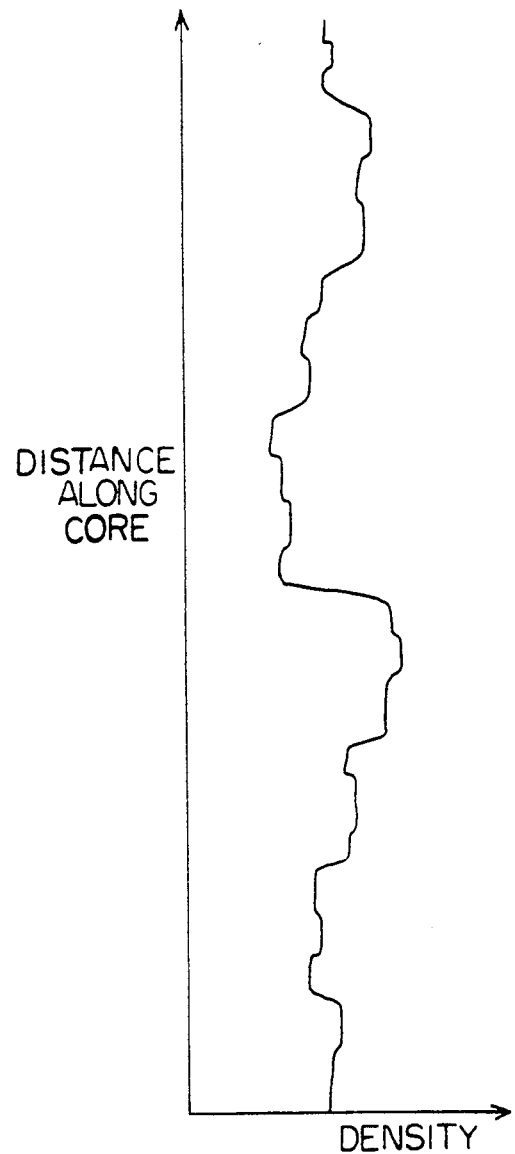

FIG. 6a shows a representative log of density (shown along the horizontal axis) versus depth as measured by a conventional density-logging instrument in a wellbore. FIG. 6b shows a comparable synthetic log of density versus distance along a core sample from the same well, made by measuring the density of slices in the core sample using the method of the invention. As clearly shown, highly improved resolution is provided by use of the method of the invention to derive density values at closely-spaced intervals along the length of the core sample. The additional information thus provided can be very useful in the search for oil and gas or in better production of existing formations.

Each of these uses of the invention makes use of the fact that according to the invention the density of a core sample of unknown composition can be accurately determined. As described above in connection with the Wellington et al article, the prior art allows determination of the density by CT scanning only when the material of the formation is already known. Accordingly, if for example residual oil or foams are present, or if the formation has become infiltrated with drilling mud or the like, the prior art is not capable of providing accurate density values. According to the invention, however, areas of the formation which are mud infiltrated can be accurately imaged, as the mud can be differentiated from varying materials which may exist within the formation. Thus, though the prior art Wellington et al article may suggest using CT scanning for generating a "synthetic log" which has much greater resolution than conventional well logging tools, such a synthetic log provided according to the teachings of the Wellington et al article is incapable of distinguishing between various materials which may be present in the core.

Having now described the method of the present invention in identifying the relative photoelectric and Compton scattering contributions to total X-ray scanning attenuation, and the use of the change in total X-ray attenuation together with the total attenuation at one of the energies to calculate the bulk density of a sample of interest, and the numerous uses which can be made of the density values thus determined, it is to be understood that various modifications and changes may be made to such method without departing from the spirit and scope of the invention as set forth in the appended claims.

We claim:

1. A method for generating a high resolution log of a core sample, accurately responsive to the bulk density of the material(s) of the core sample, comprising the steps of:

(a) selecting a first plurality of samples of a first variety of materials having different known densities, the materials of said first plurality of samples having relatively low atomic numbers, such that said samples attenuate X-rays incident thereon due to Compton scattering;

(b) irradiating each of said first plurality of samples in turn with at least first and second beams of X-rays, from sources emitting beams of X-rays at differing energies;

(c) employing detector means to collect X-rays of said beams passing through said samples;

(d) measuring amounts of X-rays collected by the detector means to determine the attenuation of the beams of X-rays of differing energies by each of the first plurality of samples;

(e) determining the parameters defining a linear relation between the attenuation of the X-rays due to Compton scattering in the first plurality of samples and the bulk densities of the samples;

(f) selecting a second plurality of samples of a second variety of materials having different known densities, the materials of said second plurality of samples having relatively high atomic numbers, such that said second plurality of samples attenuate X-rays incident thereon due to both Compton scattering and photoelectric absorption;

(g) irradiating each of said second plurality of samples in turn with at least first and second beams of X-rays from sources emitting beams of X-rays at differing energies;

(h) employing detector means to collect X-rays passing through said second plurality of samples;

(i) measuring the amount of X-rays collected by the detector means to determine the attenuation of the beams of X-rays of differing energies by each of the second plurality of samples;

(j) determining parameters defining a linear relation between the attenuation of X-rays due to photoelectric absorption in the second plurality of samples and the energy of the X-rays;

(k) using the linear relation between the attenuation of X-rays due to photoelectric absorption and the energy of the X-rays determined in step (j), and the linear relationship between the absorption of X-rays due to Compton scattering in a material sample and the bulk density of the material of the sample determined in step (e), to define a linear relation defining the bulk density of the materials of the second plurality of samples as a function of the measured total attenuation of the two beams of X-rays at two different energies by the given material; and (l) successively determining the bulk densities of a plurality of regularly spaced cross-sectional slices of the core sample by:

(1) irradiating each of the slices of the core sample with first and second beams of X-rays from sources emitting beams of X-rays at two differing energies;

(2) employing detector means to collect X-rays passing through the slices of the sample of interest;

(3) measuring the X-rays collected to determine the total attenuation of the beams of X-rays by each slice of the sample of interest; and (4) employing the relationship defined in step (k) to determine the bulk density of each slice of the core sample; and (m) displaying the successive values for the bulk density of each slice of the core sample determined in step (l) (4) to provide a density log of the core sample.

2. The method of claim 1, wherein said step (e) of determining parameters defining a linear relation between the attenuation of the beams of X-rays of differing energies by each of the first plurality of samples due to Compton scattering is carried out by determining values for the parameters a1, a2, b1 and b2 in the following expressions:

$$CT_c^{e1} = (a1)\rho - b1;$$

and $$CT_c^{e2} = (a2)\rho - b2,$$

in which:

$CT_c^{e1}$ and $CT_c^{e2}$ are quantities indicative of the attenuation of X-rays at energies e1 and e2 due to Compton scattering in said first plurality of samples; and $\rho$ represents the bulk density of the corresponding sample.

3. The method of claim 2, wherein said step (j) of determining parameters defining a linear relation between the attenuation of beams of X-rays of two different energies due to photoelectric absorption in the materials of said second plurality of samples is performed by determining values for the parameters c and d in the following expression:

$$CT_p^{31} = (c)(CT_p^{e2}) - d$$

in which:

$CT_p^{e1}$ and $CT_p^{e2}$ are quantities indicative of attenuation of X-rays at energies e1 and e2 due to photoelectric absorption in particular ones of said second plurality of samples, and in which $CT_p^{e1}$ and $CT_p^{e2}$ are determined by solution of the following equation:

$$CT_t = CT_p^{e1} - CT_p^{e2} + a3(\rho) - b3$$

in which:

$\Delta CT_t$ is the difference between measured values representing the total X-ray attenuation of the two beams of X-rays of energies e1 and e2 by ones of said second plurality of samples, $$a3 = a1 - a2.$$

and $$b3 = b1 - b2.$$

4. The method of claim 3, wherein said step (1) (4) of determining the bulk density $\rho$ of the sample of interest is performed by solution of the following linear equation defined in step (k):

$$\rho = \Delta CT_t - f(CT_t^{e'}) + g)/h$$

in which:

f, g, and h are constants determined in step (k) with respect to said second plurality of samples of materials of known density $\rho$, with respect to a beam of X-rays of a particular energy $e'$;

$\Delta CT_t$ is the difference between measured values representing the total X-ray attenuation of two beams of X-rays of different energies e1 and e2 by the sample of interest, measured in step (1)(3); and $CT_t^{e'}$ is a measured value representing the attenuation of one of the two beams of X-rays of energy $e'$ by the sample of interest.

5. The method of claim 1, comprising the further steps of:

(n) performing said step (1) with respect to a number of subsections of each slice of the core sample of interest; (o) carrying out said steps (1) and (n) repetitively with the sources and detector means disposed in differing positions with respect to the each cross-section of the core sample;

(p) generating a plurality of computed tomographic images of the slices of the core sample of interest, employing the values for the bulk density of the plural subsections of the slices of the core sample which are determined in each performance of step (n); and (q) employing the values for the bulk density of individual subsections of each of the slices of the core sample to determine the densities of the constituents of said subsections of the slices of the core sample.

6. A method for determining the disposition of constituents in a porous rock sample, comprising the steps of (1) forming an image of a cross-section of the sample in which the pixels of the image correspond to the density of corresponding sections of the sample, and (2) identifying said constituents and the materials of the rock sample, responsive to their relative densities in said image, said step (1) comprising performance of preliminary steps (a)–(c) as follows:

(a) determining parameters defining at least one first linear relation describing the attenuation of X-rays due to Compton scattering in a sample as a function of the density of the sample, by:

(i) irradiating a first plurality of samples of materials of relatively low atomic weight and known bulk density with a first beam of X-rays from a source of X-rays of a first energy;

(ii) irradiating said first plurality of samples with a second beam of X-rays from a source of X-rays of a second energy;

(iii) collecting X-rays of said first and second beams passing through said first plurality of samples on detector means;

(iv) determining the attenuation of the X-rays of the first and second beams by the first plurality of samples; and (v) determining the parameters in said at least one first linear relation responsive to the measured attenuation of the X-rays of the first and second beams by the first plurality of samples;

(b) determining parameters in a second linear relation defining the attenuation of X-rays at two different energies due to photoelectric absorption as a function of the energy of the X-rays, by:

(i) irradiating a second plurality of samples of materials of relatively high atomic weight and known bulk density with a first beam of X-rays from a source of X-rays of a first energy;

(ii) irradiating said second plurality of samples with a second beam of X-rays from a source of X-rays of a second energy;

(iii) collecting X-rays of said first and second beams passing through the samples of second plurality on detector means;

(iv) determining the attenuation of the X-rays of the first and second beams by the second plurality of samples; and (v) determining the parameters in said second linear relation responsive to the measured attenuation of the X-rays of the first and second beams by the second plurality of samples;

(c) employing the parameters of the linear relations determined in steps (a) and (b) to determine parameters defining a third linear relation describing the bulk density $\rho$ of each of said second plurality of samples in relation to the measured attenuation of the first and second beams of X-rays thereby;

(d) thereafter determining the bulk density $\rho$ of a plurality of sections of the sample oi interest by:

(i) irradiating the sample of interest with a first beam of X-rays from a source of X-rays of a first energy;

(ii) irradiating the sample of interest with a second beam of X-rays from a source of X-rays of a second energy;

(iii) separately collecting X-rays of said first and second beams passing through the sections of the sample of interest on detector means;

(iv) determining the attenuation of the X-rays of the first and second beams by the sections of the sample of interest; and (v) employing the measured attenuation of the first and second beams to solve the third linear relation defined in step (c) for the bulk density $\rho$ of each section of the sample of interest;

e) performing said step (d) repetitively, with the sources and detector means disposed at different positions with respect to the sample of interest during each performance of steps (d)(i) and (d)(ii); and (f) employing the values for the bulk density $\rho$ of the sections of the sample determined in each performance of step (d)(v) to generate a computed tomographic image of a cross-section of the sample of interest in which each pixel of the image corresponds to the density of the corresponding section of the sample; and said step (2) comprising the step of correlating the densities of known constituents of such porous rock samples with the relative densities exhibited by the pixels of the image of the section as determined in each performance of step (d).

7. The method of claim 6 wherein said linear relation defined in step (c) takes the form of the following equation:

$$\rho = (\Delta CT_t - fCT^{e'} + g)/h$$

wherein:

$\rho$ = bulk density of a particular sample;

$\Delta CT_t$ = a quantity representing the difference in measured total attenuation of two beams of X-rays of different energies by said particular sample;

$CT^{e'}$ = a quantity representative of the measured total attenuation of one of said beams of X-rays at an energy $e'$ by said particular sample; and $f$, $g$, and $h$ are parameters determined in said step (c) with respect to said second plurality of samples.

8. The method of claim 6, wherein said at least one linear relation defining the attenuation of X-rays due to Compton scattering in said first plurality of samples of step (a) takes the form:

$$CT_c^{e'} = (a')\rho - b'$$

wherein:

$CT_c^{e'}$ = a quantity representing the measured total attenuation of a beam of X-rays of energy $e'$ by a particular one of said first samples due to Compton scattering;

$a'$ and $b'$ = parameters dependent on the energy $e'$ of the beam of X-rays; and $\rho$ = measured bulk density of the particular sample.

9. The method of claim 6, wherein said linear relation between attenuation of X-rays at two different energies e1 and e2 due to photoelectric absorption of step (b) takes the form:

$$CT_p^{e1} = (c)CT_p^{e2} - d$$

wherein:

$CT_p^{e'}$ = a quantity representing attenuation of X-rays of a particular energy $e'$ due to photoelectric absorption in a sample of a material; and c and d are parameters which do not vary with the material of the sample.

10. The method of claim 6 wherein said detector means comprises a number of separate detector elements for simultaneously detecting X-rays passing through a like number of sections of the sample of interest.

11. The method of claim 6 wherein said steps (1) and (2) are performed repetitively at intervals of time during which said porous rock sample is experimentally exposed to conditions approximating those found in an exploration region from which said sample was taken, and comprising the further steps of comparing the images generated in successive performances of step (f) to monitor movement of said constituents through said sample.

12. The method of claim 6, wherein said steps (1) and (2) are performed with respect to sections of an elongated core sample at specified locations therealong, to determine variation in the disposition of said constituents in said core along its length.

13. The method of claim 12, wherein said core sample is maintained under conditions approximating those in the subterranean structure from which the core sample was withdrawn, one or more of said constituents are introduced into said core at a predetermined point, and images are formed repetitively at intervals of time, to monitor movement of said constituents through said core sample.

14. A method of generating a synthetic density log of an elongated core sample of unknown constituents, comprising the steps of:

(a) irradiating a plurality of samples comprising of materials of low atomic weight with first and second beams of X-rays of differing energy, and measuring the attenuation of the beams of X-rays by the samples;

(b) irradiating a second plurality of samples, comprising materials of higher atomic weight with first and second beams of X-rays of differing energies, and measuring the attenuation of the beams of X-rays by the samples;

(c) deriving a relationship for the density of a sample of interest as a function of the attenuation of beams of X-rays of two or more differing energies;

(d) irradiating the core sample at intervals along its length with first and second beams of X rays of differing energy, and measuring the attenuation of the beams of X-rays by the core sample;

(e) employing the relationship derived in step (c) to calculate the density of the core sample at said intervals along its length; and (f) displaying the calculated values for the density of the core sample versus the corresponding displacement along the sample.

15. The method of claim 14 wherein said relationship derived in step (c) takes the form of the following equation:

$$\rho = (\Delta CT_t - fCT^{e'} + g)/h$$

wherein:
- $\rho$ = bulk density of a particular sample;
- $CT^{e'}$ = a quantity representing the difference in measured attenuation of beams of X-rays of two different energies by said particular sample;
- $CT^{e'}$ = a quantity representative of the measured attenuation of X-rays of one of said energies $e'$ by said particular sample; and
- f, g, and h are parameters determined with respect to said second plurality of samples.

* * * * *

UNITED STATES PATENT AND TRADEMARK OFFICE
CERTIFICATE OF CORRECTION

PATENT NO. : 5,164,590
DATED : November 17, 1992
INVENTOR(S) : Coles et al.

It is certified that error appears in the above-identified patent and that said Letters Patent is hereby corrected as shown below:

Column 15, line 14, beginning of equation: "$CT_p^{31}$" should be --$CT_p^{e1}$--.

Column 15, line 24, beginning of equation: "$CT_t$" should be --$\Delta CT_t$--.

Column 16, line 68, "oi" should be --of--.

Column 18, line 5, "$CT^{e'}_p$" should be --$CT_p^{e'}$--.

Column 19, line 3, "$CT^{e'}$" should be --$\Delta CT_t$--.

Signed and Sealed this

Twelfth Day of October, 1993

Attest:

BRUCE LEHMAN

*Attesting Officer*     Commissioner of Patents and Trademarks